(12) United States Patent
Haverich

(10) Patent No.: US 9,328,327 B2
(45) Date of Patent: May 3, 2016

(54) METHOD FOR PRODUCING AN ORGAN REPLICA, IN PARTICULAR A FUNCTIONAL MODEL

(76) Inventor: Axel Haverich, Hannover (DE)

( * ) Notice: Subject to any disclaimer, the term of this patent is extended or adjusted under 35 U.S.C. 154(b) by 0 days.

(21) Appl. No.: 13/696,917

(22) PCT Filed: May 10, 2011

(86) PCT No.: PCT/DE2011/001051
§ 371 (c)(1),
(2), (4) Date: Nov. 8, 2012

(87) PCT Pub. No.: WO2011/153981
PCT Pub. Date: Dec. 15, 2011

(65) Prior Publication Data
US 2013/0059280 A1    Mar. 7, 2013

(30) Foreign Application Priority Data

May 11, 2010   (DE) .......................... 10 2010 020 222

(51) Int. Cl.
*C12N 5/00*     (2006.01)
*B29C 67/00*    (2006.01)

(52) U.S. Cl.
CPC .............. *C12N 5/00* (2013.01); *B29C 67/0051* (2013.01)

(58) Field of Classification Search
CPC .. C12N 5/00; C12N 2330/30; C12N 2535/10; B29C 67/0051
USPC .......................... 434/262–275, 219; 703/1–28
See application file for complete search history.

(56) References Cited

U.S. PATENT DOCUMENTS

| 8,790,637 B2* | 7/2014 | Mistry et al. ................. 424/93.7 |
| 2008/0026464 A1* | 1/2008 | Borenstein et al. ........... 435/395 |
| 2008/0133040 A1 | 6/2008 | Boyden et al. |
| 2009/0130427 A1 | 5/2009 | Grigoropoulos et al. |

FOREIGN PATENT DOCUMENTS

| DE | 10111422 A1 | 9/2002 |
| DE | 60028616 T2 | 1/2007 |
| EP | 0989867 A2 | 4/2000 |
| EP | 1230939 A1 | 8/2002 |
| EP | 1362092 A1 | 11/2003 |
| WO | 9308506 A1 | 4/1993 |
| WO | 95250003 A1 | 9/1995 |

(Continued)

OTHER PUBLICATIONS

Ovskianikov et al "Laser printing of cells into 3D scaffolds", Biofrabrication, Mar. 10, 2010, Iopscience, Web.

(Continued)

*Primary Examiner* — Timothy A Musselman
(74) *Attorney, Agent, or Firm* — Whitham Curtis Christofferson & Cook, PC

(57) ABSTRACT

A method for designing or replicating a human or animal organ in the form of a functional model includes providing previously recorded structural-geometric data of the organ or organ part to be replicated, selecting reconstruction materials for the organ or organ part, allocating the structural-geometric data to the individually selected reconstruction materials, and carrying out a layered assembly by the model by successively applying site-selective assembly methods for at least one part of the reconstruction materials on the basis of an associated data set.

19 Claims, 5 Drawing Sheets

(56) References Cited

FOREIGN PATENT DOCUMENTS

Figure 1:

| WO | 03037606 A1 | 5/2003 |
|---|---|---|
| WO | 2007106497 A2 | 9/2007 |

OTHER PUBLICATIONS

Hollister, Scott, "Scaffold Design and Manufacturing: From Concept to Clinic", Advanced Materials, Jun. 2, 2009, pp. 3330-3342, vol. 21.
Mironov et al., "Organ printing: Tissue spheroids as building blocks", Biomaterials, Apr. 1, 2009, pp. 2164-2174, vol. 30, No. 2, Elsevier.
Harris et al., "Recent progress in CAD/CAM laser direct-writing of biomaterials", Materials Science & Engineering, Feb. 28, 2008, pp. 359-365, vol. 28, No. 3, Elsevier.
Kofidis et al., "Myocardial Restoration and Tissue Engineering of Heart Structures", Tissue Engineering, 2007, pp. 273-290, Humana Press, New Jersey.
Mironov et al., "Organ printing: computer-aided jet-based 3D tissue engineering", Trends in Biotechnology, Apr. 2003, pp. 157-161, vol. 21, No. 4, Elsevier.
Jakab et al., "Organ printing: Fiction or science", Biorheology, 2004, pp. 371-375, vol. 41, IOS Press.
Mironov, Vladimir, "Toward Human Organ Printing: Charleston Bioprinting Symposium", Asaio Journal, 2006, pp. 27-30.

* cited by examiner

METHOD FOR PRODUCING AN ORGAN REPLICA, IN PARTICULAR A FUNCTIONAL MODEL

FIELD OF THE INVENTION

The invention relates to a method for producing a replica of a human or animal organ or of a part thereof or of some other segment of a human or animal body, more particularly as a functional model for research and teaching, and to the organ or body-segment replica produced in this manner and the use thereof.

BACKGROUND

For a long time, attempts have been made to replicate biological tissue to imitate nature so that these structures can be used, firstly, as models for research and, secondly, for medical purposes in patients suffering from tissue loss. For the associated research area, the term "tissue engineering" has been established internationally.

For example, EP 1362092 B1 discloses a cell patch based on a collagen nonwoven support. The support composed of a wound-care nonwoven having collagen fibrils makes possible a culture of cells applied thereto, which partly allows self-organization thereof. The artificial tissue patch thus obtained can be used for the study of drug effects, the effect of growth factors on cell culture, or surgically as augmentation material. It is still not possible for more complex tissue structures to be obtained in this manner.

EP 0989867 B1 discloses a basic method for producing an acellularized and reseeded native collagen matrix as tissue transplant. However, the patent does not provide for active vascularization, and so the supply to the cells of the freshly produced bioartificial material is a problem.

This is overcome by the teaching of EP 1230939 B1, in which a primarily vascularized, acellularized, autologous, allogeneic or xenogeneic tissue matrix having at least one vascular branch is used in vitro or in vivo for the reseeding. However, the new, bioartificial tissue is bound to the vascular structure of the matrix taken as a basis and requires a human or animal starting matrix.

The course mostly pursued to date of providing a native extracellular matrix in acellularized form, of artifically replicating it, for example with a polymer, or of forming it from native material and of then allowing said matrix to remodel in the body or of then preseeding said matrix using an external method, limits the variability of the obtainable tissue to a large extent, since complex tissues are technically not manageable.

The modeling, or replication or new construction, of entire organs is therefore in its infancy and is limited to those organs having a not too complex tissue structure which is relatively uniform at least in certain areas. Specific results have been achieved to date in the direction of skin, intestine and bladder, as shown by DE 600 28 616 T2 for example.

SUMMARY

In contrast, the object of the invention is to be able to provide nature-imitating replicas of entire organs by using biological materials, including cells. The replicas shall exhibit natural functions and thus be able to serve as models in research and teaching (functional models). The natural functions shall be observable at least in an artificial environment (in vitro) under gentle conditions. Furthermore, the replicas shall stimulate transplantation research.

The object is achieved by a method as claimed in claim 1, an organ or segment replica as claimed in claim 12 and the use thereof as claimed in claim 15. Further advantageous embodiments of the invention are characterized in the dependent claims.

To achieve the object, the invention takes a completely new approach. The invention utilizes developments in rapid prototyping technology and especially in stereolithography and methods derived therefrom for the three-dimensional construction of increasingly finer, even biological, structures in order to specifically position in space selected materials for the construction of an organ functional model, such that a replica of an organ or of a segment, for example in the form of a model, is produced. The materials selected for the replication, including cells, matrix materials, such as collagen, fibrin, polysaccharides, etc., are navigated to very specific positions on the basis of previously obtained data of the organ or segment to be replicated, which are present in data sets and form a kind of mapping.

The invention utilizes the self-organization ability of cells and biological materials. This is relied on in the case of, inter alia, already known coating methods, when living cells in a suspension are added to a support and cultured there. There, too, cell masses form by themselves, and this can be supported by, for example, the addition of factors {including growth factors).

For the purposes of the invention, "filling method" means that hollow spaces generated using the method (during prototyping) are filled with further materials, liquids, supporting solids, etc. In this connection, cells can also be positioned, for example when cells are introduced into the hollow spaces which are situated in a culture medium which does not allow the cells to sediment (e.g., a semisolid medium—containing agar or gelatin).

Free spaces—lumina, cavities—present in the organs to be replicated can be utilized for support scaffolding, by firstly placing there a support material which can be removed later from the organ replica or model which has become inherently more stable—for example, as a result of self-organization of the biological materials. The support materials can, for example, be gels or, for example, sugar polymers which are known in the research area and preferably readily resolubilizable.

The general method according to the invention is elucidated below in greater detail.

In principle, the method according to the invention for producing a replica of a human or animal organ or of a part thereof or of some other body segment is characterized by steps a) to d), and this does not exclude the possibility of adding further steps, for example steps serving to stabilize the newly obtained tissue, or rinsing steps.

The term "organ parts" is understood to mean, for example, individual pulmonary lobes, individual hepatic lobes, individual skin areas, blood vessels, etc. In detail, the method always comprises (explicitly or implicitly) the steps of:
  a) providing precaptured structural geometric data of the organ, organ part or segment to be replicated;
  b) selecting reconstruction materials for the organ or the part to be replicated, comprising at least the following groups: at least one material for the reconstruction of an extracellular matrix, at least one type of organ-specific cells,
  c) assigning the structural geometric data to the individual selected reconstruction materials;
  d) assembling the model layer-by-layer through successive application of site-selective assembly methods for at least some of the reconstruction materials on the basis of an associated data set, wherein only site-selective assembly methods are applied or they are combined with further methods such as coating methods or filling methods.

In step a), precaptured structural geometric data of the organ, organ part or segment to be replicated are provided.

"Structural geometric data" are understood to mean the detailed geometry of the original body part, i.e., organ or segment, to be replicated, in the form of 3D data. In this connection, structural geometry is the geometry, i.e., the spatial shape, of the biological structure, including in terms of its details inside. In principle, it is first necessary for the biological character of the organ, organ part or segment serving as template to be determined at every point in space. Owing to the actual resolution of the methods used for this purpose, very small cubic spatial zones are concerned de facto, not spatial points, even if points are talked about below. For simpler models, it is also possible to deliberately coarsen the resolution in order to thus simply the replica.

The "structural geometric data" thus form a data set composed of information relating to a material type or a material class assigned to its three-dimensional positioning in space, viz., specifically within the envelope of the organ, organ part or segment to be replicated. The data can be captured or be present in one total data set or in multiple individual data sets, as will be explained below. The minimal requirement for the data of the data sets is therefore the form $(M_i; x_i; y_i; z_i)$ with i=1 to n; n $\in$ {N}, where M is a value for the character of the material and x, y, and z are the spatial coordinates.

Obtaining the structural geometric data is, in this respect, a method step preceding the actual construction or replication method, since these data do not have to be newly collected for each construction of a replica. On the contrary, it is presently intended that standard organ shapes, for example of heart, lung, kidney, liver, pancreas, muscles, teeth, are replicated, and so, in each individual case, one-off data collection can suffice. It is of course possible to capture multiple standard types, for example the same organ in different stages of development or growth or in sex-specific development.

Natural organs are required as template, i.e., for the capture of the structural geometric data. Preferably, the method is applied to hearts, cardiac parts and vessels.

In principle, the structural geometric data can be determined noninvasively on a living body, for example spectroscopically, including by means of MRT (magnetic resonance tomography), by means of echography or computed tomography. A further possibility consists in preparing a natural organ and obtaining the structural geometric data from the mostly isolated, prepared organ. In the case of animal organs, they are obtained from, for example, a slaughterhouse. For human organs, organ parts or other segments which are classically not referred to as organs, but which can be replicated using the method according to the invention, body donations or healthy organs from clinical pathology are a possibility. For the replication of a heart to produce a replica, i.e., a model or implant according to the invention, what is required is, for example, at least one heart from a woman, one heart from a man and one heart from a child. In addition to human organs, it is also possible to use animal organs and to replicate a very wide variety of different animal organ models, for example it is possible to use hearts from pigs, gorillas or chimpanzees.

Therefore, in one development of the invention, the organ to be replicated and serving as template is prepared, the organ is impregnated with a sectioning medium, for example a wax or resin, and sections, preferably ultramicrotome sections, are produced from the organ, with staining being carried out before or after sectioning to determine the various biological materials. Preferably, an immunohistological stain is used.

In a particularly preferred embodiment of the invention, the structural geometric data are then obtained from the stained section images by identifying the various materials of these section images and recording their coordinates. With regard to the individual section, planar coordinates are directly obtained, related to the section sequence spatial coordinates.

For the staining, a very wide variety of different standard methods, which can also be combined in order to obtain a complete image, can be considered. The staining methods are known to a person skilled in the art in the field, to a biologist, biochemist or physician, and therefore do not need to be explained here in detail. Suitable methods appear to be, inter alia, histological methods, such as hematoxylin and eosin staining (HE), overview staining for distinguishing different tissue structures. By this means, assignment of the spatial coordinates for extracellular matrix (ECM) and cells is already obtained, and the latter can be classified on the basis of their appearance. Also suitable appears to be PAS staining (periodic acid-Schiff reaction) for depicting polysaccharide-containing cell and tissue constituents. Further suitable appear to be, for example, Ladewig staining (staining of connective tissue, discrimination of collagen fibers (blue), nuclei (brown), erythrocytes (orange) and musculature (blue)), azan staining, Goldner staining, elastic van Gieson staining, Gomori or silver staining, to name but a few.

Using immunohistochemical (immunohistological) techniques, it is possible for tissues and cells to be differentiated more precisely. This is achieved by means of specific antibodies which are themselves labeled with fluorescent dyes, enzymes, particulate material (e.g., gold particles) or with radioactive isotopes. Alternatively, it is possible to use specific primary antibodies which can be detected by means of labeled secondary antibodies. Labeling which has been carried out is detected differently depending on its nature. A person skilled in the art selects appropriate methods in detail on the basis of his or her expert knowledge.

The material boundaries can now be defined, for example visually and by manual input of the visually determined boundaries within the individual section images. What is obtained is a total data set containing the spatial coordinates of individual selected or contemplated materials (connective tissue, different cells, fluid regions, possibly empty spaces, etc.). Assignment can be carried out both manually, i.e., by visual inspection and manual data input, and in a (semi) automated manner, with or without visual/manual postprocessing and verification.

In a particularly preferred embodiment of the invention, automatic assignment can be carried out on the basis of measured values from the section images. More particularly, color values, degrees of darkness (darkness/brightness detection), measured intensities or contrast values of the individual points of the stained sections are suitable for the assignment.

To set up the total data set or the data sets for the geometric data of individual determined materials, a person skilled in the art can use further methods and criteria on the basis of his or her expert knowledge.

Directly during capture or subsequently in a separate step, multiple materials present in the natural organ, i.e., in the template preparation to be replicated, which cannot be or are not to be replicated individually in the model can be pooled into one material class. For instance, there may be individual specific cells which are present in a cell mass and cannot be provided for the replication, i.e., the model construction. The entire area can then be depicted or replicated in a simplifying manner using similar cells which are selected on the basis of their belonging to a particular type of cells, for example epithelial cells, connective tissue cells, neurons or muscle cells.

In the manner described above, the structural geometric data for the natural template can first be obtained as a complete data set relating to all (identifiable) starting materials, and they can then be converted by correlation into a data set for the structural geometric data of the replica, i.e., for the precise three-dimensional positioning of each individual reconstruction material, or the reconstruction materials can be directly assigned during the determination of the structural data to identified original materials. In both cases, what is obtained is a total data set for the reconstruction materials in a precise, three-dimensional assignment that is used for the subsequent material assembly of the replica.

In one development of the invention, the data of the total data set can be assigned to the sub-data sets for the reconstruction materials on the basis of their color values, contrast values or other optical data.

"Reconstruction materials" are understood here to mean the materials which are present in the replica instead of the original materials identified by the template analysis. In some cases, they are exactly the same or corresponding materials, as in the template, and in other cases, they are materials which are specifically selected differently. For example, positions ("spatial points", see above) showing endothelial cells in the image of the template organ can also be occupied by endothelial cells in the model. Alternatively, it is also possible to use a particular different polymer as reconstruction material for collagen. All spatial points for which the collected data set indicates collagen would then be occupied by the chosen reconstruction polymer in the model or in the replica of the organ or segment.

After the pure capture of the origin materials in step a), it is therefore necessary in any case in a further step b) to select specific reconstruction materials for the organ or the part of the organ to be replicated. According to the invention, these ought to comprise at least the following groups:
1. at least one material for the reconstruction of an extracellular matrix. Here, it needs to be a structural material, for example collagen, a collagen-like or collagen-forming mass which solidifies or can be subsequently solidified, a fiber-forming mass, a hyaluronic acid or hyaluronic acid derivative mixture, some other biopolymer, a synthetic polymer, more particularly one which is remodelable, i.e., resorbable, and naturally substitutable in the body.
2. at least one type of organ-specific cells, in fact preferably multiple types of organ-specific cells, if multiple types are present in the organ or organ part. Organ-specific cells are firstly understood to mean all cells which are found in the organ or body segment (including cells not restricted to the specific organ). In detail, these are both the parenchymatous cells (e.g., the hepatocytes of the liver) and the cells forming the stroma of an organ (e.g., connective tissue cells). A first type of cells may preferably be muscle cells, preference being given to smooth muscle cells (SMC), striated muscle cells and cardiac muscle cells, a second type of cells may preferably be epithelial cells, preference being given to dermal epithelial cells, intestinal epithelial cells, pneumocytes (alveolar epithelial cells), endothelial cells. Further cells which can be used are neurons (motor neurons, sensory neurons and interneurons, and the glial cells (astrocytes, oligodendrocytes, Schwann cells and satellite glial cells (amphicytes)), and connective tissue/supporting tissue cells (fibroblasts, myofibroblasts, tendinocytes, chondrocytes, osteoblasts, adipocytes, pericytes, etc.).

Another possibility are stem cells, which differentiate later in situ with the aid of particular further substances—including differentiation factors, for example particular hyaluronic acids.

In step c) of the method according to the invention, the structural geometric data are assigned to the individual reconstruction materials selected for the model assembly. This can be carried out explicitly in an additional step after the capture of the true materials, or reconstruction materials can be directly assigned to the section images on the basis of particular assignment criteria. In any case, the reconstruction materials are identified and assigned on the basis of measured values from section images, however they were obtained, more particularly on the basis of color values, degrees of darkness, measured intensities or contrast values.

As already explained above, the reconstruction materials can differ from the original biological materials determined for the particular site. This takes into account, inter alia, the complexity of the original, the exact replication of which does not appear possible. Nevertheless, situated in most organs are relatively large spatial regions of a uniform substance or cell class, which spatial regions can be replicated using a uniform reconstruction material. For the construction of the replica, it is also possible to mix cells with materials which are intended to promote the formation of a cell mass—unlike in the template.

For the replication or model construction, it is possible to use, for example, particular cell mixtures, mixtures of cells and media, mixtures of cells and factors, etc. The same also applies to providing the extracellular matrix. Here, it is likewise possible to use materials other than what can be identified in detail from the template (the section). These mixed reconstruction materials are then assigned to the area of use envisioned in the model on the basis of the structural geometric data, i.e., on the basis of the data or data sets determined for this purpose. Essential to the invention is the assignment of the materials, i.e., a specific spatial assignment between the determined starting material and a reconstruction material envisioned therefor at the same spatial site in the replica, i.e., the model, the implant, the prosthesis.

For the correlation between the structural geometric origin data and the data for the reconstruction materials, a person skilled in the art can use known mathematical methods and set up further criteria for the correlation.

For example, it is possible to additionally use manually determined spatial coordinates—these can be, for example, coordinates for particularly important key positions within the replica—as key data for a correlation.

Within the section planes, boundaries between the reconstruction materials can be determined by interpolation or functional description between predefined key data.

After completion of the preliminary work according to steps a) to c), the practical assembly of the replica is carried out according to step d) using site-selective assembly methods known per se. Generally, a plurality of these assembly methods will be required for the construction of a replica. Together, the assembly methods which have been selected form a prototyping method for the replica or the model.

On the basis of the "map" of the organ or organ part to be replicated that was obtained by the capture, weighting and assessment of the structural geometric data, the selected reconstruction materials are now navigated to their assigned position in the following step.

In step d) of the method according to the invention, the layer-by-layer assembly is carried out through successive application of site-selective assembly methods for at least some of the reconstruction materials on the basis of respectively assigned data sets. As already mentioned in step b), this comprises at least at least one matrix material and the at least one type of organ-specific cells. Further materials can be introduced into the raw model using other, additional methods—for example by coating. The data sets required for the site-specific assembly methods (prototyping method) can be present as matrices, or in another mathematical treatment suitable for the control of the desired assembly method. In general, the captured structural geometric data can be present as sub-data sets, for example for particular spatial regions to be processed using a particular assembly method, or for particular reconstruction materials, or in the form of a total data matrix which is specifically accessed for the control of the assembly methods. According to the invention, only site-selective assembly methods can be applied or they can be combined with further methods such as coating methods or filling methods. For particular materials identified in the section, empty spaces can remain in the model, for example for fluids such as blood (within vessels) or if there is also a hollow space in the original organ, for example in the lung. In the case of primary layer-by-layer assembly, it is also possible to leave empty spaces where subsequently further assembly methods, for example the coating of the model obtained so far, are used. Furthermore, instead of the ultimate reconstruction materials for the model, it is possible to firstly use provisional substitute materials, which are subsequently replaced by other reconstruction materials.

In a preferred embodiment, reconstruction material-specific data sets or data matrices for the construction of the replica are first created from the total data set. However, this is primarily a purely technical measure for obtaining separate data sets for method control for the various assembly methods, which will be described below. The devices for the assembly methods can also access in each case the total data set, if this is technically possible and appropriate.

The more precise assignment between starting and reconstruction materials and the correlation of the data can be carried out in detail in different ways by a person skilled in the art on the basis of his or her expert knowledge.

At least one of these assembly methods can be a stereolithographic method or a method further developed therefrom, and such methods include, in particular, two-photon or multiphoton polymerization.

Classic stereolithographic methods are known from, for example, WO95/25003 or WO 93/08506. This involves a method for producing moldings from a liquid material to be solidified by irradiation in a bath of said material, primarily in a layer-by-layer assembling manner, by irradiation of the bath surface. With the aid of a laser beam focusable on various spatial points of the bath, this form of stereolithography was further developed, and so now, specific polymerization within the bath is possible simply by shifting the laser focus. With regard to the description of this method, reference is made to DE 101 11 422 A1.

Using the method of two-photon polymerization, it is also possible to realize very fine structures, as occur in biological systems, for example in organs. Reference is made to the publication "Two-photon polymerization technique for microfabrication of CAD-designed 3D scaffolds from commercially available photosensitive materials", Journal of Tissue Engineering and Regenerative Medicine, 2007, 1, 443-449, A. Ovisianikov, S. Schlie, A. Ngezahayo, A. Haverich and B. N. Chichkov, which is hereby incorporated into the disclosure content of this application by reference.

Especially for the layer-by-layer replication (the assembly) of the extracellular matrix, preference is given to applying a stereolithographic method and particular preference is given to applying two-photon or multiphoton polymerization.

The site-selective assembly method used for the layer-by-layer replication, i.e., the assembly, of the cellular layers and regions is preferably a Laser Induced Forward Transfer (LIFT) of the cells.

In this connection, it is possible to evenly apply the desired cell type or the cells cultured as reconstruction material onto the LIFT support in a two-dimensional manner and to transfer individual cells from there, point by point, to the replica plane currently being assembled. The data matrix specifying the positions to be transferred within the cells to be coated onto the support is a submatrix of the reconstruction data total matrix, which was in turn obtained from the raw data total matrix of the starting model.

The cells presented on the LIFT support can, if desired, be provided with a preferred orientation. They can be transferred while preserving an orientation.

In an alternative embodiment, the extracellular matrix material can also be brought to its destination in the replica by means of LIFT. It is particularly preferred when a complete layer/section plane of the replica is put together in each case from the various reconstruction materials using LIFT.

With the Laser Induced Transfer method, it is possible to specifically move very small particles, molecules and especially cells in a translational movement from a starting point to a target point using a laser and the energy thereof. The cells to be moved are, for example, coated in a thin layer in suspension onto a glass support, which is irradiated from the reverse side with the (focused) laser. The transport is supported by auxiliary particles, for example particular nanoparticles or an elemental noble metal, for example gold, in a thin layer, which vaporizes owing to the laser energy and catapults onwards from the support the cells or other materials to be transported.

A more precise description of the LIFT method can be found in, inter alia, US 2009/0130427 A1 or WO 03/037606, which, with regard to the description of this assembly method according to the invention, are incorporated into the disclosure of this application.

Surprisingly, it is possible with the LIFT method to achieve an exact layer-by-layer assembly of the cellular regions of the replica or of the model.

The assembly can be carried out in planar layers or alternatively in spherical layers, though the assembly using the LIFT method is preferably carried out in planar layers.

In a preferred embodiment, a solid foundation is firstly obtained by starting the layer-by-layer assembly on a selected section surface having a large enough cross-section and carrying it out from this cross-sectional surface in both transverse directions with respect to the section surface in an alternate or successive (sequential) manner.

In a particularly preferred exemplary embodiment of the invention, the lumina are stabilized by firstly filling them with a soluble material or a dimensionally stable material removable under mild conditions, for example a polymer. This is preferably done, during the site-selective assembly, by introducing a solid, mechanical stability-imparting polymer as reconstruction material at the position of the lumina—i.e., at positions at which the organ to be replicated is gas- or fluid-filled, more particularly within blood vessels. Thus, a vascular branch becomes additional support scaffolding for the model (the replica). After completion of the model or the replica and after the biological materials have attained sufficient inherent stability, the stabilizing material is removed. The stabilizing material can be gels or water-soluble polymers known in the research area, for example particular polysaccharides or sugar polymers. In direct spatial connection with the lumina, it is possible to include those areas which can be applied later within the lumina by coating. Within a vascular branch, it is for example readily possible to subsequently apply vascular inner coatings, for example a layer of endothelial cells. This inner coating of vessels is done using methods known per se, for example from a cell suspension.

The structural materials used for the replica and especially the reconstruction material used for the reconstruction of the extracellular matrix are preferably a precursor for a polymer solidifiable by energy exposure and particularly preferably by radiation. This can be a synthetic polymer or a polymer based on natural starting substances. Long-term stable, mechanically robust nonresorbable polymers or alternatively biocompatible polymers which are bioresorbable or else resorbable and are remodelable in the body are used depending on the use of the replica. The polymers can be used as such, i.e., in a homogeneous phase, or in a mixture with one or more biopolymers or, prior to solidification, with biopolymer monomers or oligomers. Preferred reconstruction materials contain hyaluronic acid and/or collagen, for example; also usable in mixtures for reconstruction materials are ECM mixtures, for example Matrigel®. Fibrin can be obtained as matrix material from preferably photopolymerizable fibrinogen, as known in principle in the prior art. Fibrin can also be transferred in portions with the LIFT method, polymerizing or gelling classically (enzymatically) in situ.

In preferred exemplary embodiments, cells of the following groups are used as reconstruction materials:

muscle cells (smooth muscle cells, striated muscle cells, cardiac muscle cells), epithelial cells (intestinal epithelial cells, dermal epithelial cells, intestinal epithelial cells, endothelial cells, pneumocytes, endothelial cells) neurons (motor neurons, sensory neurons, interneurons, and glial cells (astrocytes, oligodendrocytes, Schwann cells, satellite glial cells (amphicytes)), connective tissue cells (fibroblasts, tendinocytes, chondrocytes, osteoblasts, adipocytes, myofibroblasts, pericytes)

and stem cells. The list is exemplary and not complete. Further specific functional cells of an organ which make up the parenchyma can likewise be introduced into the model, for instance hepatocytes for hepatic tissue; beta cells (insulin cells), alpha cells (glucagon cells), delta cells (somatostatin cells) for pancreatic tissue, etc.

Further reconstruction materials which may possibly be added, i.e., optionally, are ions, amino acids, peptides, proteins, lipids, carbohydrates, nucleic acids, growth factors, differentiation factors, nutrients, hormones and/or chemotactic agents.

In one development of the invention, the aforementioned additives and possibly further or other substances are introduced into the (organ) replica by means of coating methods and/or rinsing after the assembly steps or after individual assembly steps or introduced together with the cells during the assembly steps.

Other than by the method, the object of the invention is also achieved by a replica of a human or animal organ, of a part thereof or of some other segment of the human or animal body that is obtainable in particular using the method according to the invention and that is notable for a nature-imitating assembly having at least one polymer as substitute for extracellular matrix of the organ, for cells and/or cell masses composed of at least one cell type and for organ-specific gas-, fluid- or blood-filled free spaces. In particular, the assembly is of course organ-specific.

Preferably, the replica contains at least one first type of cells that are muscle cells and at least one second type of cells that are epithelial cells.

Further preferably, cells that are connective tissue cells and neurons are present. The introduced cells later form their own matrix and form an intercellular substance, and so no undesired hollow spaces at all remain.

The polymer which forms the reconstruction material for the extracellular matrix or is present in said reconstruction material is preferably a biologically degradable polymer or a polymer which is reconstructable (remodelable) in a human or animal body, as described above.

The replica according to the invention can firstly serve as an illustrative model and as a functional model for research, for example for the study of medicamentous effects or the influence of all other manipulations on organs, whether of a surgical, pharmacological or gene-technology nature. However, a further use according to the invention is also the use as a prosthesis or implant in a human or animal body.

The invention will now be more particularly elucidated below using exemplary embodiments and figures. These elucidations are intended to serve solely to illustrate the invention and not to restrict the invention in its entirety.

DESCRIPTION OF THE DRAWING FIGURES

Figure 2:
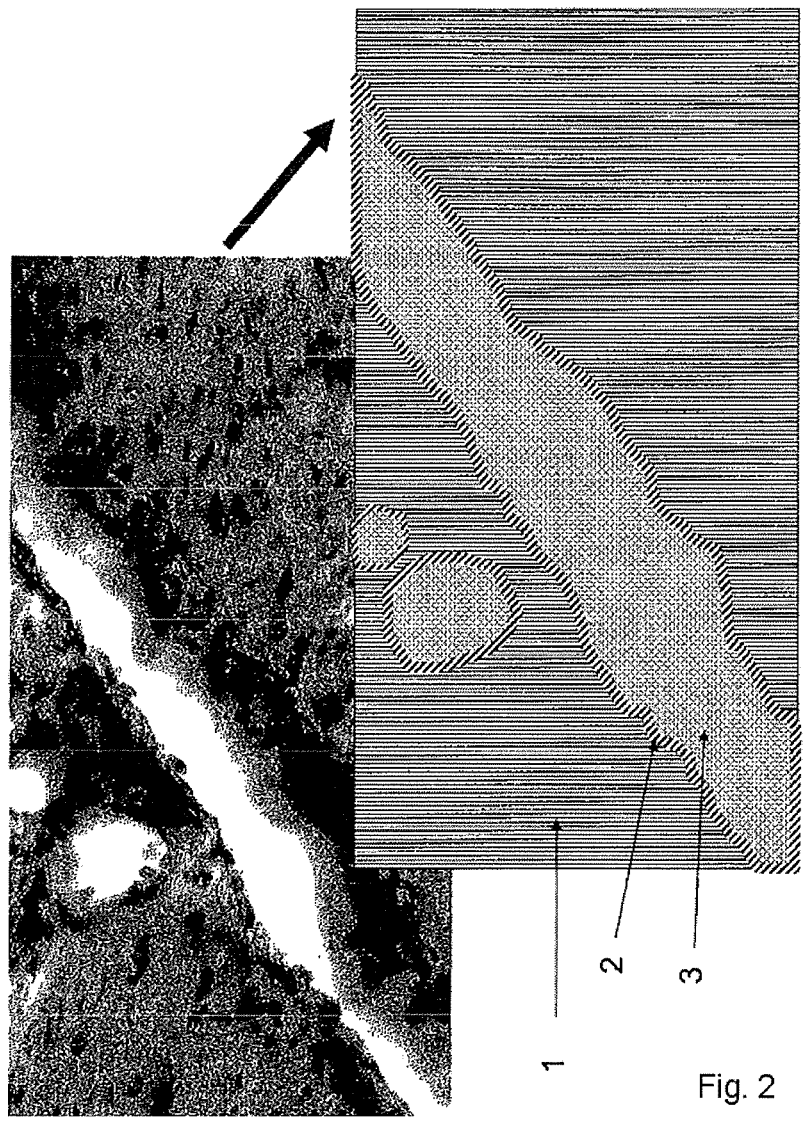
Figure 3:
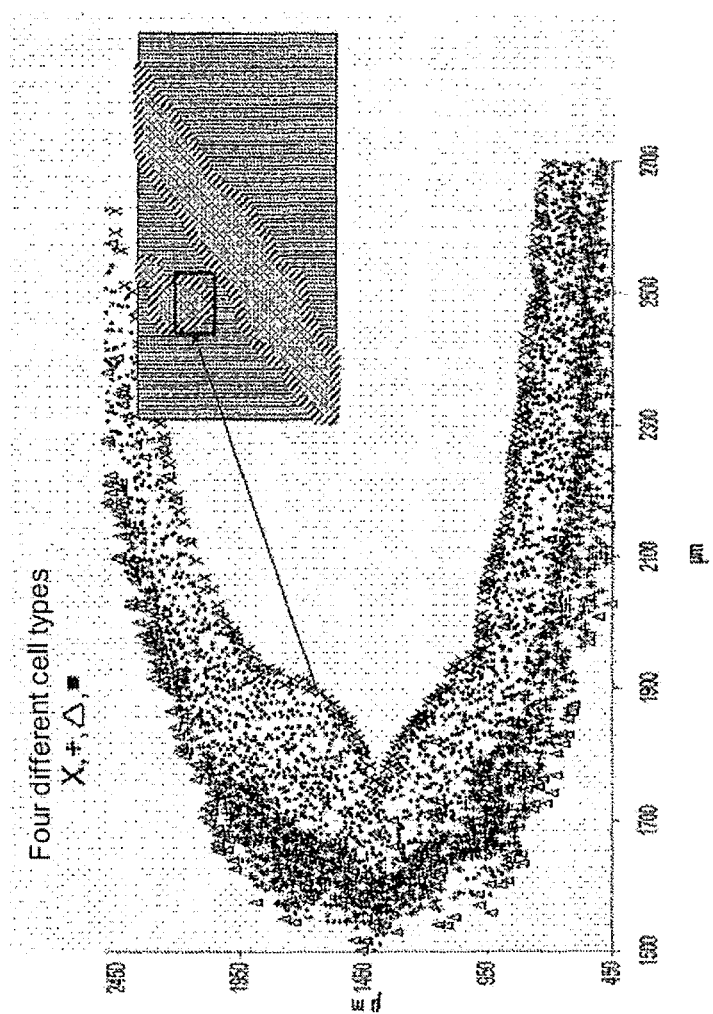

For this purpose, reference is made to the figures. The following are shown:

FIG. 1 a histologically stained ultramicrotome section of a region of a porcine heart;

FIG. 2 a schematic diagram of structural identification on a greatly enlarged section region;

FIG. 3: graph containing spatial coordinates for various identified cell types for a cutout from the structural identification in FIG. 2 (see assignment)

Figure 4:
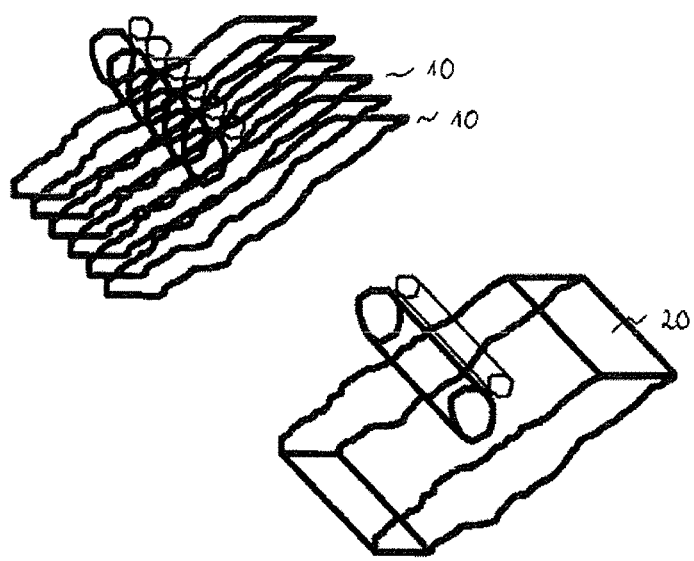
Figure 5:

FIG. 4: the method in principle for 3D reconstruction from individual layers or individual section images;

FIG. 5: a computer-generated virtual organ section image.

DESCRIPTION

In FIG. 1, it can be seen how the sections of an organ preparation that have been stained with an HE stain allow the precise spatial assignment of the biological materials (cells, extracellular matrix, vascular lumen) present in the template organ. The planar image provides on the computer, via the sequence and the thickness of the sections, a three-dimensional assignment of all selected, i.e., contemplated, origin materials. The ultramicrotome section can also be stained "multicoloredly" with a plurality of successively applied methods. This can facilitate the assignment to the reconstruction materials. It also allows the automatic identification of particular cells and materials present in the template organ on the basis of color values of the section image.

FIG. 2 shows a simplified depiction of structure identification. Here, a greatly enlarged cutout was chosen from the ultramicrotome section of a porcine heart. In this example, the precise—two-dimensional, planar with regard to the section plane—position of muscle cells 1, vascular walls 2 and vascular lumina 3 was determined from the section image and saved in a planar image. Superimposing such planar images produces, on the computer, the three-dimensional structural geometric data required for the replication, i.e., the assembly of the model.

FIG. 3 shows a graph containing the spatial coordinates of particular cells, captured according to type, in a cutout region from the structure identification in FIG. 2. The cutout to which the graph is assigned is identified by the frame in the superimposed section image 10 from FIG. 2. Proceeding from an onset or origin, the Cartesian coordinates within the section area are reported in micrometers (μm). The four identified and assigned cell types are identified schematically by four different symbols. Within a grid, whose coarseness or fineness in the nanometer to micrometer range is defined beforehand, a material, i.e., in this case a cell type, can be assigned to each grid point or to each grid area within the section plane. Correspondingly, the grid points or grid areas at which vacuoles, lumina or fluid regions are supposed to be present are determined on the model—and thus defined for the reconstruction. These regions can be transitionally represented by substitute materials, for example supporting materials, during the reconstruction. Supporting materials can be, for example, gelatin or other, removable polymers. However, another possibility are reconstructions in which lumina do not have to be filled, if they, for example, are surrounded by inherently dimensionally stable materials, for example particular matrix materials such as collagen, such that the hollow space is fixed, i.e., the organ reconstruct does not collapse at this site during the layer-by-layer reconstruction.

The cell assignment symbols in FIG. 3 have the following meaning:

TABLE 1

| Symbol | "Identified" cell type/material type | Material type selected for the reconstruction |
|---|---|---|
| X | Endothelial cells | Endothelial cells (cultured in a standardized or (recipient) specific manner) |
| ■ | SMCs parallel to the image plane | SMCs - not orientated |
| + | SMCs perpendicular to the image plane | SMCs - not orientated |
| Δ | Other cells, predominantly fibroblasts | Fibroblasts |
| Empty (luminal) | (Lumen) | Optionally stabilizing material |

The layered assembly can be seen more closely in FIG. 4. The individual planar images 10 are layered so as to produce the complete three-dimensional data set, illustrated here in the 3D structure 20.

In FIG. 5, it can be seen how the structure of a histologically captured organ segment can look on the computer. For identification of the section structure, an organ slice was selected. In this slice, a multiplicity of superimposed section data are already utilized. The spatial data which have been captured and assigned to reconstruction materials are used for the control of the prototyping methods for the replica, for example a functional model, i.e., they are used in the preferred examples for the two-photon polymerization of polymers for the extracellular matrix and for the LIFT of the various cell types. At present, it is possible for up to three cell types to be positioned in parallel in one LIFT run.

EXAMPLES

1. Construction of an Organ Segment Traversed by Vessels

Firstly, the structure of the vascular branch present in the organ part to be replicated is determined. The structural geometric data for the vascular branch are used for two-photon polymerization of the supporting structure of the branch. In the example, this hollow tube-like structure, which can be branched, is produced from polyethylene glycol diacrylate or PEG tetraacrylate by photopolymerization in the presence of a photoinitiator. This method is known per se.

Alternatively, the natural proteins fibrinogen and thrombin can be polymerized to form fibrin. The method would then accordingly be conducted stereolithographically, as described in principle above.

The structure produced is rinsed.

Subsequently, the structure is rotated in the target region of a LIFT apparatus such that the outsides of the vascular branch created from the polymer are precisely covered with cells which are known for these positions from the structural geometric data. This procedure is repeated until the layer-by-layer application of cells has been completed and the organ construct has been obtained. For example, muscle cells (cardiac muscle cells), connective tissue cells (fibroblasts) and neurons are used for the assembly of cardiac regions.

Finally, the inner surfaces of the vascular branch (the luminal lining of the vessels) are covered by means of a coating method with the cells (in this case: endothelial cells) to be provided there according to structural geometric data. For this purpose, these cells are distributed in the vascular internal spaces in suspension or in a low-viscosity hydrogel and the structure is rotated or swiveled until adhesion of a cellular layer on the vascular interior. The above-described assembly with cells and possibly other materials and the subsequent coating preferably always takes place under perfusion in order to immediately supply the freshly applied cells with nutrients and to transport away metabolic products. For this purpose, blood or nutrient solution is conducted through the vessels of the model. Therefore, the advantage of this example, which starts with the assembly of the vessels, is also that, from the start, a perfusion means which replicates natural conditions well is achieved.

2. Assembly of an Organ Part in Layers Corresponding to Section Planes

For this example, the suborgan model is assembled in planar layers, wherein all the reconstruction materials required therefor are introduced successively for each layer using site-selective assembly methods.

The modeling starts on a middle cross-sectional plane of the organ in order to obtain a large supporting surface for the assembling functional model. Using the selected prototyping methods, both cells and structural materials, i.e., polymers or extracellular matrix, are applied to a base plate of glass or stainless steel. This is carried out similar to a printing process or copying process. In accordance with the structural data, the cells are "imprinted" in each case using the LIFT method, i.e., brought on the base plate to the position calculated for this organ plane. For this purpose, the LIFT glass plate, to which the cells to be transferred are applied, is arranged parallel to the base plate at a defined distance. The cell coating is located on the side facing the base plate, the laser on the side facing away from the base plate. After coating with a cell type at the positions predefined by the structural geometric data, the glass plate is switched for LIFT transport of another cell type.

For the matrix material, the liquid precursor material is layered over the plane currently being displayed and irradiated at the points at which matrix polymer is to be applied. Afterwards, rinsing is carried out.

The following layer of the functional model is applied in the same way as described above. Lastly, the submodel is removed from the base plate and turned, so that the layer-by-layer assembly can be continued in the opposite direction.

Alternatively, the assembly of an organ part is carried out from top to bottom or vice versa.

For example, epithelial cells (alveolar epithelial cells (pneumocytes)) and connective tissue cells (chondrocytes and fibroblasts) are used for the assembly of pulmonary regions.

The invention claimed is:

1. A method for producing a model of a human or animal organ or of a part thereof or of some other segment of a human or animal body, comprising the steps of:
   a) providing precaptured structural geometric data of the organ, organ part or segment to be replicated, which structural geometric data form a data set composed of information relating to a material type or a material class assigned to a three-dimensional positioning in space, wherein the structural geometric data are obtained from stained section images, or are determined noninvasively on a living body;
   b) selecting reconstruction materials for the organ, organ part or segment to be replicated, comprising at least one material for the reconstruction of an extracellular matrix and at least one type of organ-specific cells;
   c) assigning the structural geometric data to individual selected reconstruction materials of said reconstruction materials selected in said selecting step on the basis of measured values from section images;
   d) assembling the model layer-by-layer through successive application of site-selective assembly methods for at least some of the reconstruction materials which include both the at least one material for the reconstruction of the extracellular matrix and the at least one type of organ-specific cells based on an associated data set, and wherein a site-selective assembly method used for a layer-by-layer replication of cellular layers and regions is a Laser Induced Forward Transfer (LIFT) of the cells.

2. The method as claimed in claim 1 wherein individual reconstruction material-specific data sets for construction of the model are obtained from the total data set of the structural geometric data.

3. The method as claimed in claim 1 wherein manually determined spatial coordinates are included in said associated data set.

4. The method as claimed in claim 1 wherein a site-selective assembly method applied for the layer-by-layer replication of the extracellular matrix is a stereolithographic method or Laser Induced Forward Transfer (LIFT).

5. The method as claimed in claim 1 wherein said assembling step is carried out in planar layers or spherical layers.

6. The method as claimed in claim 1 wherein the layer-by-layer assembly of the model is carried out from a selected section surface in both transverse directions with respect to the section surface in an alternate or successive manner.

7. The method as claimed in claim 1 wherein lumina are stabilized by filling them with a soluble polymer or a polymer removable under mild conditions.

8. The method as claimed in claim 1 wherein said at least one material for the reconstruction of the extracellular matrix is or includes a polymer solidifiable by energy exposure.

9. The method of claim 8 wherein said energy exposure is radiation exposure.

10. The method of claim 8 wherein said polymer is present in a mixture with one or more biopolymers or biopolymer monomers or oligomers.

11. The method as claimed in claim 1 wherein said at least one type of organ specific cells are selected from the group consisting of epithelial cells, muscle cells, connective tissue cells, neurons and stem cells.

12. The method as claimed in claim 1 further comprising introducing one or more of ions, amino acids, peptides, proteins, lipids, carbohydrates, nucleic acids, growth factors, differentiation factors, nutrients, hormones, chemotactic agents, or other additives into or on the model by one or more of coating methods or rinsing after the assembling step or after individual assembly steps in said assembling step or by being introduced with the at least one type of organ-specific cells during the assembling step.

13. The method of claim 1 wherein said reconstruction materials include one or more of ions, amino acids, peptides, proteins, lipids, carbohydrates, nucleic acids, growth factors, differentiation factors, nutrients, hormones, and chemotactic agents.

14. The method of claim 1 wherein said stained section images are immunohistologically stained section images.

15. A model of a human or animal organ, of a part thereof or of some other segment of a human or animal body, produced by the process of
   a) providing precaptured structural geometric data of the organ, organ part or segment to be replicated, which structural geometric data form a data set composed of information relating to a material type or a material class assigned to a three-dimensional positioning in space, wherein the structural geometric data are obtained from stained section images, or are determined noninvasively on a living body;
   b) selecting reconstruction materials for the organ, organ part or segment to be replicated, comprising at least one material for the reconstruction of an extracellular matrix and at least one type of organ-specific cells;
   c) assigning the structural geometric data to individual selected reconstruction materials of said reconstruction materials selected in said selecting step on the basis of measured values from section images;
   d) assembling the model layer-by-layer through successive application of site-selective assembly methods for at least some of the reconstruction materials which include both the at least one material for the reconstruction of the extracellular matrix and the at least one type of organ-specific cells based on an associated data set and wherein a site-selective assembly method used for a layer-by-layer replication of cellular layers and regions is a Laser Induced Forward Transfer (LIFT) of the cells,
   said model having
   a nature-imitating assembly having at least one polymer as a substitute for extracellular matrix of the organ,
   at least one of cells and cell masses composed of at least one cell type, and
   organ-specific gas-, fluid- or blood-filled free spaces.

16. The model as claimed in claim 15, containing at least one first type of cells that are muscle cells and at least one second type of cells that are epithelial cells.

17. The model as claimed in claim 15, wherein the at least one polymer is a biologically degradable polymer or a polymer which is remodelable in a human or animal body.

18. A method of treating a subject, comprising the steps of:
   producing a model of a human or animal organ, vessel, or a part thereof or of some other segment of a human or animal body, by the process of
   a) providing precaptured structural geometric data of the organ, organ part or segment to be replicated, which structural geometric data form a data set composed of information relating to a material type or a material class assigned to a three-dimensional positioning in space, wherein the structural geometric data are obtained from stained section images, or are determined noninvasively on a living body;

b) selecting reconstruction materials for the organ, organ part or segment to be replicated, comprising at least one material for the reconstruction of an extracellular matrix and at least one type of organ-specific cells;

c) assigning the structural geometric data to individual selected reconstruction materials of said reconstruction materials selected in said selecting step on the basis of measured values from section images;

d) assembling the model layer-by-layer through successive application of site-selective assembly methods for at least some of the reconstruction materials which include both the at least one material for the reconstruction of the extracellular matrix and the at least one type of organ-specific cells based on an associated data set, and wherein a site-selective assembly method used for a layer-by-layer replication of cellular layers and regions is a Laser Induced Forward Transfer (LIFT) of the cells; and e) implanting said model in said subject.

19. The method of claim 18 wherein said model is a heart patch.

* * * * *